United States Patent
Schlenger et al.

(10) Patent No.: US 12,053,326 B2
(45) Date of Patent: Aug. 6, 2024

(54) APPARATUS AND METHOD FOR AUTOMATIC ULTRASOUND SEGMENTATION FOR VISUALIZATION AND MEASUREMENT

(71) Applicant: Verdure Imaging, Inc., Stockton, CA (US)

(72) Inventors: Christopher Schlenger, Stockton, CA (US); Tamas Ungi, Stockton, CA (US)

(73) Assignee: Verdure Imaging, Inc., Stockton, CA (US)

( * ) Notice: Subject to any disclaimer, the term of this patent is extended or adjusted under 35 U.S.C. 154(b) by 0 days.

(21) Appl. No.: 18/195,832

(22) Filed: May 10, 2023

(65) Prior Publication Data
US 2023/0320700 A1    Oct. 12, 2023

Related U.S. Application Data

(63) Continuation of application No. 17/569,797, filed on Jan. 6, 2022, which is a continuation-in-part of
(Continued)

(51) Int. Cl.
*A61B 8/08* (2006.01)
*A61B 8/00* (2006.01)

(52) U.S. Cl.
CPC ............ *A61B 8/483* (2013.01); *A61B 8/4254* (2013.01); *A61B 8/4263* (2013.01); *A61B 8/466* (2013.01)

(58) Field of Classification Search
CPC ..... A61B 8/483; A61B 8/4254; A61B 8/4263; A61B 8/466; A61B 8/085; A61B 8/5223; A61B 8/5253
See application file for complete search history.

(56) References Cited

U.S. PATENT DOCUMENTS

| 9,675,321 B2 | 6/2017 | Schlenger |
| 9,713,508 B2 | 6/2017 | Schlenger |

(Continued)

FOREIGN PATENT DOCUMENTS

| EP | 3705049 A1 | 9/2020 |
| JP | 2014221175 A | 11/2014 |

OTHER PUBLICATIONS

Yu-Shun Wong et. al; Is Radiation-Free Ultrasound Accurate For Quantitative Assessment of Spinal Deformity in Idiopathic Scoliosis (IS): A Detailed analysis With Eos Radiograpy on 952 Patients; Ultrasound in Med. & Biol., vol. 45, No. 11, pp. 2866-2877, Elsevier Inc. Amsterdam, Netherlands.

(Continued)

*Primary Examiner* — Bo Joseph Peng
(74) *Attorney, Agent, or Firm* — Bamert Regan PLLC; Raymond W. Armentrout

(57) ABSTRACT

A system and method for performing ultrasound scans is provided. One embodiment of the ultrasonagraphic system acquires sonogram information from a series of ultrasonic scans of a human subject. The series of ultrasound scans are taken over a portion of interest on the human subject which has their underlying bone structure or other ultrasound discernable organ that is under examination. The data from the series of scans are synthesized into a single data file that corresponds to a three-dimensional (3D) image and/or 3D model of the underlying bone structure or organ of the examined human subject.

18 Claims, 9 Drawing Sheets

Related U.S. Application Data application No. 16/813,469, filed on Mar. 9, 2020, now Pat. No. 11,246,569.

(56) References Cited

U.S. PATENT DOCUMENTS

| | | | |
|---|---|---|---|
| 2004/0254460 A1* | 12/2004 | Burcher | A61B 5/6843 |
| | | | 600/437 |
| 2005/0182319 A1* | 8/2005 | Glossop | A61B 6/5247 |
| | | | 600/424 |
| 2006/0094958 A1* | 5/2006 | Marquart | A61F 2/4609 |
| | | | 600/434 |
| 2007/0081709 A1* | 4/2007 | Warmath | G09B 23/285 |
| | | | 382/128 |
| 2007/0167784 A1* | 7/2007 | Shekhar | A61B 6/032 |
| | | | 600/443 |
| 2010/0179428 A1* | 7/2010 | Pedersen | G09B 23/286 |
| | | | 600/443 |
| 2013/0289406 A1 | 10/2013 | Schlenger | |
| 2015/0133785 A1 | 5/2015 | Schlenger et al. | |
| 2016/0228190 A1* | 8/2016 | Georgescu | A61B 34/10 |
| 2016/0328998 A1* | 11/2016 | Pedersen | A61B 8/4245 |
| 2017/0360401 A1 | 12/2017 | Rothberg et al. | |
| 2022/0125517 A1 | 4/2022 | Zimmermann et al. | |

OTHER PUBLICATIONS

"Scolioscan Air"—The First of its Kind Palm-Sized 3D Ultrasound Imaging System Brings Accurate, Safe and Cost-Efficient Mass Screening to Schools and Anywhere in the Community; The Hong Kong Polytechnic University, Mar. 4, 2020; Department f Biomedical Engineering.

Pileun Kim, et. al; SLAM-driven robotic mapping and registration of 3D point clouds, ResearchGate publication; article in Automation in Construction, May 2018, 34 pages.

Will Schroeder, et. al; The Visualization Toolkit, An Object-Oriented Approach To 3D Graphics, Chapter 5 "Basic Data Representation", Edition 4.1, Jul. 2018.

3D Scanning, Wikipedia website, https://en.wikipedia.org/w/index.php?title=3D_modeling&oldid=942604827, 7 pages, May 2, 2023.

3D Modeling, Wikipedia website, https://en.wikipedia.org/w/index.php?title=3D_scanning&oldid=939462491, 18 pages, May 2, 2023.

Ungi et al, Automatic Spine Ultrasound Segmentation for Scoliosis Visualization and Measurement, Transactions on Biomedical Engineering, 2020, 8 pages.

* cited by examiner

APPARATUS AND METHOD FOR AUTOMATIC ULTRASOUND SEGMENTATION FOR VISUALIZATION AND MEASUREMENT

PRIORITY CLAIM

This application is a Continuation of, and claims priority to, copending U.S. application Ser. No. 17/569,797, filed on Jan. 6, 2022, entitled Systems and Methods For Automatic Ultrasound Segmentation For Visualization And Measurement, which is a Continuation In Part of, and claims priority to, copending U.S. application Ser. No. 16/813,469, filed on Mar. 9, 2020, entitled Systems and Methods For Automatic Ultrasound Segmentation For Visualization And Measurement, which are hereby incorporated by reference in their entirety for all purposes.

BACKGROUND OF THE INVENTION

In the arts of human body visualization, and in particular visualization of a human spine, X-ray images and computed tomography (CT) scans have been fairly effective in acquiring image data of human body parts, and in particular, human bone structures such as the spine. Magnetic resonance imaging (MRI) is another tool to obtain image data of human body parts.

However, X-ray machines, MRI machines and CT scanning machines are very expensive to acquire and to operate. X-ray images present graphical information on a limited two-dimensional plane. MRI is unsatisfactorily slow and provides low resolution images of bone structures.

Further, X-ray imaging and CT scanning use ionizing radiations (X-rays) that may be harmful to the human subject, particularly if the human subject must undergo repeated testing over a long duration of time. For example, a human subject suffering from advancing scoliosis (a curvature of the spine) must, from time to time, be examined to ascertain the extent and/or change in the scoliosis of their spine. Repeated exposure to radiation during periodic examinations may be harmful to such human subjects.

Other less potentially harmful devices are available for acquiring human subject information are available. For example, ultrasound devices project sound waves into the human subject and detect returning sound wave echoes to generate an image, referred to as a sonogram. Ultrasound devices used in ultrasonographic systems produce sound waves at a frequency above the audible range of human hearing, which is approximately 20 kHz. Sound waves between 2 and 18 Mhz are often used for ultrasound medical diagnostic applications. At present, there are no known long-term side effects from interrogating the human body with ultrasound waves.

However, an ultrasound scan can cover only a relatively small part of the human subject's body with each scan. Further, the sonogram is a relatively narrow image, covering a relatively small cross section of only a few inches. And, objects identified in the sonogram may often be blurry. For example, five hundred to one thousand sonogram images must be captured to acquire a sufficient amount of image data for analysis of a full human spine. Accordingly, legacy ultrasound scanners are inadequate for acquiring image information for the human subject's body when a large area of the human subject must be examined, such as the human subject's spine, because the sonogram images are too small and a large number of sonogram images cannot be easily analyzed to arrive at any meaningful information about the condition of the examined human subject.

Sonogram scan images can be evaluated as a two dimensional (2D) grid of image pixels corresponding to the width and the length of a particular sonogram scan image. Each image pixel is defined by an intensity value (i.e., brightness). The intensity value may be associated with a particular structure that is detected in a sonogram scan. For example, an image pixel with a high value (wherein the image pixel appears as a visually dark pixel) may be associated with bone tissue of the scanned patient. Image pixels with low intensity values may be associate with other types of soft tissue. Accordingly, sonogram scan images are known to provide visual indications of a patient's tissue, such as their bone structure.

The depth of each pixel in a sonogram scan image may be known or may be determinable. Accordingly, each pixel in a sonogram scan image and its associated intensity can be associated with a voxel in a 3D volume. Since high intensity values of the sonogram scan image pixels may be associated with bone structure, the voxels in a 3D volume having high intensity values may be used to define a 3D model of the surface of the patient's bone along the scanned line of the sonogram scan image.

In 3D computer graphics, 3D modeling is referred to as the process of developing a mathematical representation of any surface of an object (either inanimate or living) in three dimensions via specialized software. The product is called a 3D model. Three-dimensional (3D) models represent a physical body using a collection of points in 3D space, connected by various geometric entities such as triangles, lines, curved surfaces, etc. Being a collection of data (points and other information), 3D models can be created manually, algorithmically (procedural modeling), or by scanning. Their surfaces may be further defined with texture mapping. (See Wikipedia, Feb. 25, 2020.)

An example purpose of a scanner is to create a 3D model. This 3D model consists of a point cloud of geometric samples on the surface of the subject. These points can then be used to extrapolate the shape of the subject (a process called reconstruction). For most situations, a single scan will not produce a complete model of the subject. Multiple scans, even hundreds, from many different directions are usually required to obtain information about all sides of the subject. These scans have to be brought into a common reference system, a process that is usually called alignment or registration, and then merged to create a complete 3D model. This whole process, going from the single range map to the whole model, is usually known as the 3D scanning pipeline. (See for example Wikipedia, Feb. 6, 2020, and Kim et. al; "SLAM-driven Robotic Mapping And Registration Of 3D Point Clouds," 2018; and Lorensen et. al, "The Visualization Toolkit An Object-Oriented Approach To 3D Graphics," Ed. 4.1, Chapter 5, July 2018.)

Accordingly, there is a need in the arts to more effectively acquire sonogram image data from a human subject using ultrasound devices for generation of 3D models of a patient's tissue of interest.

SUMMARY OF THE INVENTION

Embodiments of the ultrasonagraphic system provide a system and method for performing ultrasound scans. One embodiment of the ultrasonagraphic system acquires sonogram information from a series of ultrasonic scans of a human subject. The series of ultrasound scans are taken over a portion of interest on the human subject which has their underlying bone structure or other ultrasound discernable organ that is under examination. The data from the series of scans are synthesized into a single data file that corresponds to a three-dimensional (3D) image and/or 3D model of the underlying bone structure or organ of the examined human subject.

BRIEF DESCRIPTION OF THE DRAWINGS

The components in the drawings are not necessarily to scale relative to each other. Like reference numerals designate corresponding parts throughout the several views.

DETAILED DESCRIPTION

Embodiments of the ultrasonagraphic system 100 provides a system and method for acquiring sonogram information from a series of ultrasonic scans of a human subject. The series of ultrasound scans are taken over a portion of interest on the human subject which has their underlying bone structure or other ultrasound discernable organ that is under examination. The data from the series of scans are synthesized into a single data file that corresponds to a three-dimensional (3D) image and/or 3D model of the underlying bone structure or organ of the examined human subject.

The disclosed ultrasonagraphic system 100 will become better understood through review of the following detailed description in conjunction with the figures. The detailed description and figures provide merely examples of the various inventions described herein. Those skilled in the art will understand that the disclosed examples may be varied, modified, and altered without departing from the scope of the inventions described herein. Many variations are contemplated for different applications and design considerations; however, for the sake of brevity, each and every contemplated variation is not individually described in the following detailed description.

Throughout the following detailed description, examples of various ultrasonagraphic systems 100 are provided. Related features in the examples may be identical, similar, or dissimilar in different examples. For the sake of brevity, related features will not be redundantly explained in each example. Instead, the use of related feature names will cue the reader that the feature with a related feature name may be similar to the related feature in an example explained previously. Features specific to a given example will be described in that particular example. The reader should understand that a given feature need not be the same or similar to the specific portrayal of a related feature in any given figure or example.

The following definitions apply herein, unless otherwise indicated.

"Substantially" means to be more-or-less conforming to the particular dimension, range, shape, concept, or other aspect modified by the term, such that a feature or component need not conform exactly. For example, a "substantially cylindrical" object means that the object resembles a cylinder, but may have one or more deviations from a true cylinder.

"Comprising," "including," and "having" (and conjugations thereof) are used interchangeably to mean including but not necessarily limited to, and are open-ended terms not intended to exclude additional, elements or method steps not expressly recited.

Terms such as "first", "second", and "third" are used to distinguish or identify various members of a group, or the like, and are not intended to denote a serial, chronological, or numerical limitation.

"Coupled" means connected, either permanently or releasably, whether directly or indirectly through intervening components.

Figure 1:
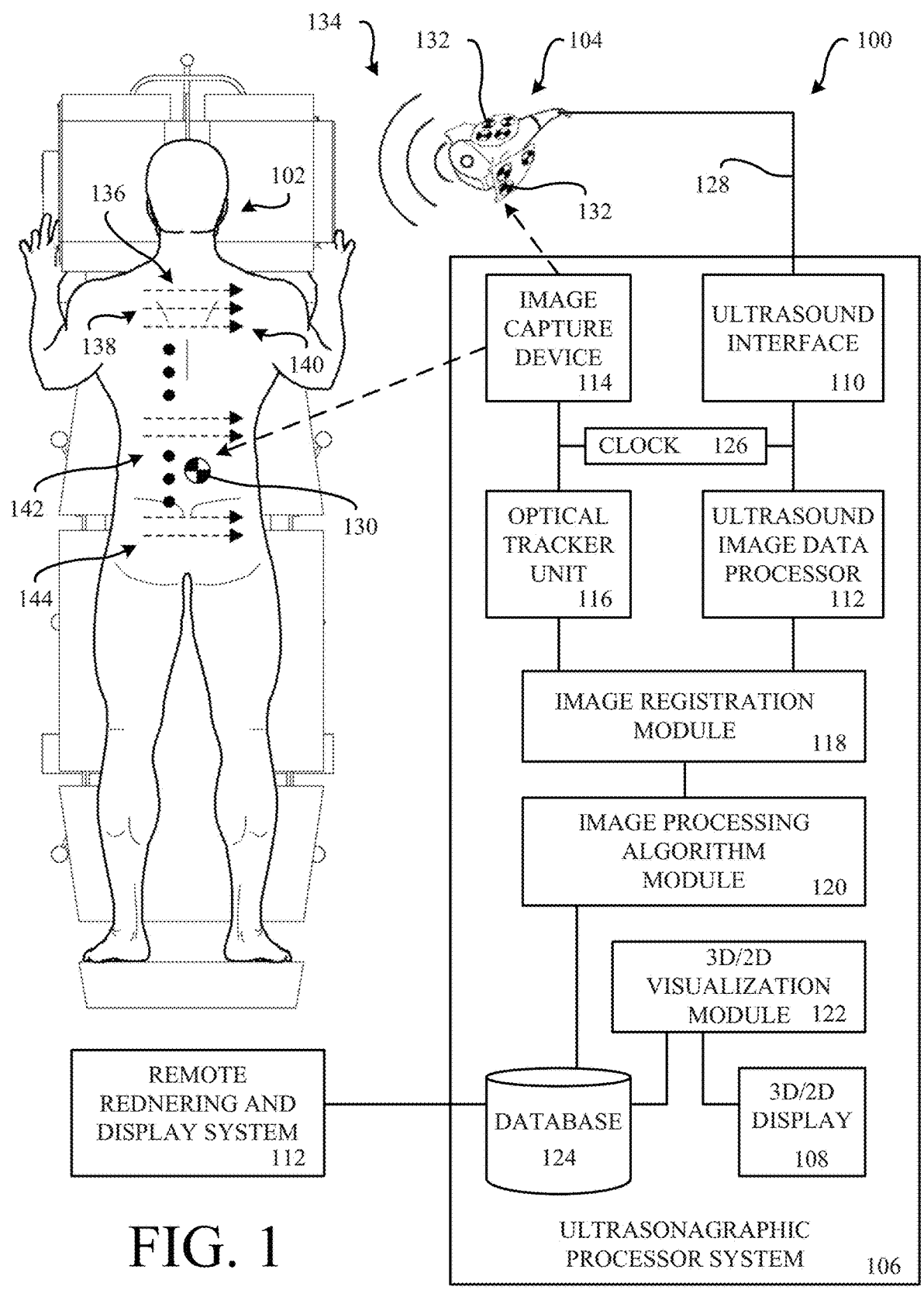
FIG. 1 is a schematic view of an ultrasonagraphic system for examining and treating spinal conditions.

FIG. 1 is a schematic view of an ultrasonagraphic system 100 for acquiring 3D image information and 3D model data for bone structures or other internal organs of a human subject 102. Various examples are described herein in the context of examining and treating spinal conditions by acquiring 3D image information and 3D model data for the spine of the human subject 102. Alternatively, or additionally, two-dimensional (2D) image information and/or 2D model data may be generated by embodiments of the ultrasonagraphic system 100.

In the non-limiting example application, the ultrasonagraphic system 100 of FIG. 1 is configured to enable a practitioner to acquire ultrasound images (sonograms) of a patient's spine in real-time with ultrasound transducer probe 104. The ultrasonagraphic processor system 106, after receiving sonogram image information from a series of ultrasound scans, generates the 3D image information and/or 3D model data of the spine human subject 102 without subjecting the patient to potentially harmful ionizing radiation. Further, ultrasonagraphic system 100 of FIG. 1 enables a practitioner to acquire images of the outer cortex of a patient's spine with high resolution on a real-time or substantially real-time basis. One skilled in the art appreciates that the ultrasonagraphic processor system 106 may be used to generate 3D image and/or 3D model data for other portions of the human subject 102. In some examples, the system is optionally configured to stereoscopically display the images in three dimensions, such as with the 3D visualization module and a 3D/2D stereoscopic display 108 shown in FIG. 1.

An example embodiment of the ultrasonagraphic processor system 106 comprises an ultrasound interface 110, an ultrasound image data processor 112, at least one image capture device 114, an optical tracker unit 116, an image registration module 118, an image processing algorithm module 120, a 3D/2D visualization module 122, and a database 124. Some embodiments include an optional clock 126. The ultrasound interface 110 communicatively couples the ultrasound transducer probe 104 to the ultrasonagraphic processor system 106 via a wire-based or wireless connection 128.

In alternative embodiments, the image registration module 118, the image processing algorithm module 120, and/or the 3D visualization module may be integrated together, and/or may be integrated with other logic. In other embodiments, some or all of these memory and other data manipulation functions may be provided by using a remote server or other electronic devices suitably connected via the Internet or otherwise to a client device (not shown). The database 124 may be implemented using any suitable local and/or remote memory device or system. Depending upon the embodiment, the database 124 may be a dedicated memory system, may be part of another component or system, and/or may be a distributed local and/or remote memory system. The database 124 may also include other logic, modules and/or databases not illustrated or described herein. Other ultrasonagraphic systems 100 may include some, or may omit some, of the above-described components. Further, additional components not described herein may be included in alternative embodiments.

As conceptually illustrated in FIG. 1, the ultrasonagraphic system 100 utilizes optical tracking technology to precisely detect the location of the scanned portion of the patient relative to the ultrasound transducer probe's 104 position in 3D space. The image capture device 114 acquires image information in a space around the human subject 102 and the ultrasound transducer probe 104. The image information (interchangeably referred to herein as a camera image) is acquired in a periodic serial fashion, preferably at a rate of tens or hundreds of image frames per second. The image capture device 114 may be any suitable device that periodically captures still images or that captures video images (known in the arts to be a time sequenced series of still images). The captured image data is then communicated from the image capture device 114 to the optical tracking unit 116.

Each acquired camera image has an associated time stamp that specifies a time of camera image capture or camera image time of acquisition. The camera image capture time may be expressed in real time or by using a reference time. Time stamp information may be provided by an internal clock residing in the image capture device(s) 114. Alternatively, the clock 126 may add in time stamp information to the acquired camera images as they are being communicated from the image capture device 114 to the optical tracker unit 116.

In some embodiments, a plurality of image capture devices 114 may be used to capture camera images in a synchronized fashion. That is, the multiple image capture devices 114 provide concurrently captured camera images with the same time stamp.

The optical tracking unit 116, for each acquired image, identifies the one or more optical targets 130 that have been placed on the surface of the body of the human subject 102. Also, the optical tracking unit 116, in each acquired image, identifies the one or more optical targets 132 that have been placed on the surface of the ultrasound transducer probe 104.

Optical targets 130, 132 may be conventional, specially developed, or later developed optical targets that are discernable by the optical tracking unit 116. In some examples, the optical targets 130, 132 extend in three dimensions about three coordinate axes and include distinct optical target portions representing each axis. In other examples, the optical target 130, 132 extends in three dimensions about six axes and includes distinct optical targets representing each of the six axes. The optical targets 130, 132 may be active, such as by emitting infrared signals to the optical target, or passive, such as including retro-reflective markers affixed to some interaction device.

The optical tracking unit 116 then computes or determines the position of the ultrasound transducer probe 104 relative to the optical target 130 in 3D space for the indexed time. The position determination is based upon the identified relative location of the optical targets 130, 132 in the acquired camera image. One skilled in the art appreciates that relative location between optical targets 130, 132 can be based upon their identified location in an image. Further, orientation of the optical targets 130, 132 can be determined from an analysis of the image of the optical targets 130, 132. Accordingly, the position and orientation of the ultrasound transducer probe 104 relative to the optical target 130 can be determined.

Then, the optical tracking unit 116 determines the corresponding location on the body of the human subject 102. This determined location on the human subject 102 is interchangeably referred herein as the time indexed location information. The time indexed location information identifies the location and the time that the ultrasound transducer probe 104 was on the human subject 102. Any suitable position tracking system now known or later developed may be used by the various embodiments of the ultrasonagraphic system 100 to determine the time indexed location information.

It is worth noting that that ultrasonagraphic system 100 of FIG. 1 is configured to detect the position of the human subject 102 directly by the optical target(s) 130 positioned on the human subject 102 as opposed to merely detecting the position of a fixed object near the human subject 102, such as a chest board or other stationary reference objects. Accordingly, if during examination the human subject 102 moves or adjusts their position, the time indexed location information determined from later acquired camera images can be correlated with time indexed location information determined from earlier acquired camera images.

Additionally, or alternatively, to the optical tracking technology included in the example of FIG. 1, the ultrasonagraphic system 100 may include magnetic positioning systems or attitude heading reference systems to detect the position of the human subject 102, the ultrasound transducer probe 104, or both. For example, location and/or orientation of the ultrasound transducer probe 104 may be determined by various micro electro-mechanical devices (MEMS) such as accelerometers or the like.

Additionally, or alternatively, the ultrasonagraphic system 100 may include an infrared scanning system configured to scan illuminated objects, such as the human subject 102, in three-dimensions. The infrared scanning system may include an infrared light projector, a camera or CMOS image sensor to detect the infrared light interacting with illuminated objects, and a microchip including computer executable instructions for spatially processing scanned objects. Suitable infrared scanning systems include the Light Coding™ system included in the Kinect™ gaming system. The infrared scanning system may supplement the optical tracking device and optical targets described above or may replace them in some applications.

In practice, an operator (not shown) such as an ultrasound technician, a doctor, or another individual, operates the ultrasound transducer probe 104 in a manner that emits sonic waves 134 into the human subject 102. Within the context of acquiring echo return data, interchangeably referred to herein as sonogram information or sonogram data, the operator begins the scanning process by performing a first sonogram scan 136 over a selected location of the human subject 102. To conceptually illustrate use of an embodiment of the ultrasonagraphic system 100, examination of the spine of the human subject 102 is described. The sonogram scanning begins at a first location on the human subject 102, such as near the head of the human subject 102, and that is at a location that is to the side of the centerline of the spine of the human subject 102. The operator then moves the ultrasound transducer probe 104 in a substantially straight line across the spine of the human subject 102.

During the first sonogram scan 136, in an example embodiment, sonogram information corresponding to a plurality of serially acquired sonogram images are communicated from the ultrasound transducer probe 104 to the ultrasound interface 110. A time stamp corresponding to the time of acquiring the sonogram image is added by ultrasound transducer probe 104 to an individual sonogram image to generate time indexed sonogram image information portion. Alternatively, the clock 126 may add the time information to the acquired sonogram image to generate the time indexed sonogram information portion.

Alternatively, the ultrasound transducer probe 104 may provide a continuous stream of sonogram information (echo return data) corresponding to the return echoes detected by the ultrasound transducer probe 104 during each scan. When a stream of data corresponding to detected echoes is provided, time stamps are periodically added into and/or are associated with particular potions of the streaming echo return data. Thus, the echo return data acquired during the beginning of the scan will have an associated first time stamp that corresponds to the time of data acquisition, and later portions of the acquired echo return data will be associated with later time stamps to reflect the time that that echo return data was acquired by the ultrasound transducer probe 104.

The associated time stamp specifies a time of acquisition of the sonogram image and/or acquisition of a portion of the stream of sonogram echo data. The time indexed sonogram image and/or the time indexed sonogram echo data portion is interchangeably referred to herein as the time indexed sonogram image information portion.

The time stamps associated with the time indexed sonogram information may be expressed in real time or by using a reference time. The time stamp information may be provided by an internal clock residing in the ultrasound transducer probe 104. Alternatively, the clock 126 may add in time stamp information to the acquired sonogram information as the time indexed sonogram information is communicated from the ultrasound interface 110 to the ultrasound image data processor 112. The sonogram image time stamps have the same time reference as the corresponding time stamps associated with the time indexed camera images concurrently captured by the image capture device 114.

As is known in the arts, the ultrasound image data processor 112 processes the received sonogram information acquired during the first sonogram scan 136 into a time indexed sonogram image information portions which may be used to render the first sonogram image. The time indexed sonogram image information portions are communicated from the ultrasound image data processor 112 to the image registration module 118.

The time stamps of each of a plurality of portions of the first sonogram image are correlated with the corresponding time indexed camera images by the image registration module 118. For each of the time stamps of one of the time indexed sonogram image information portions, a corresponding camera image with the same or substantially the same time stamp is correlated with that particular time indexed sonogram image information portion. Accordingly, the location and orientation of the ultrasound transducer probe 104 relative to the target 130 on the human subject 102 during each portion of the first sonogram scan 136 is determined. That is, the location and orientation of the ultrasound transducer probe 104, and therefore the location of each time indexed sonogram image information portion on the body of the human subject 102 is determined by the image registration module 118. The location on the body of the human subject 102 is based on the location information determined from the corresponding time indexed camera image that has the same time stamp information. Accordingly, the location information for each associated location indexed sonogram image information portion identifies the location of that first sonogram image portion on the body of the human subject 102.

As one skilled in the arts appreciates, a first sonogram images generated from the first sonogram scan 136 has a relatively narrow range (width) that typically only encompasses one or more inches of width. Accordingly, after the first sonogram scan 136 has been completed, the operator shifts the position of the ultrasound transducer probe 104 downward by a predefined incremental distance (referred to herein as the "sonogram scan shift distance") for a subsequent sonogram scan. Preferably, the sonogram scan shift distance is no greater than the sonogram image width of the sonogram images acquired during the first sonogram scan 136. The operator then conducts a second sonogram scan 138 across the human subject 102.

The second sonogram scan 138 runs parallel to, or substantially parallel to, the first sonogram scan 136. One skilled in the art appreciates that some degree of overlap between the sonogram image information acquired during the second sonogram scan 138 and the first sonogram image information acquired during the first sonogram scan 136 may occur. In some situations, such an overlap in the sonogram image information is desirable. During later construction of the 3D/2D image and/or 3D/2D model data, information determined from any overlapping portions of sonogram image information is merely duplicative and can be discarded, erased, or is not used, and therefore, will not adversely impact generation of the 3D/2D image and/or 3D/2D model data. In some embodiments, the duplicative information is combined to generate enhanced sonogram image information.

The image registration module 118 then generates a plurality of location indexed sonogram image information portions based on the information received from the ultrasound image data processor 112 and the optical tracking unit 116. For each processed sonogram scan, the location indexed sonogram image information portions comprise sonogram image information for the particular portion of the sonogram scan, optional time indexing information where each time index identifies a particular time of acquisition for the associated sonogram image portion, and location information for each associated sonogram image portion that identifies the location of the image portion on the body of the human subject 102.

Similarly, a third sonogram scan 142, adjacent to the second sonogram scan 138, may be acquired. The process of conducting a continuing series of sonogram scans 140 continues, with each successive sonogram scan being separated by the previous sonogram scan by the predefined sonogram scan shift distance. The process of conducting the series of parallel sonogram scans continues over the portion of the human subject 102 that is being examined. In the illustrative example of examining the spine of the human subject 102, the sonogram scanning process may end with the last sonogram scan 144 that corresponds to a scan of the lower end of the spine of the human subject 102.

The scanning process above was described as a parallel series of sonogram scans 136 to 144 which were oriented perpendicular to the orientation of the spine of the human subject 102. This scanning sequence is convenient because the operator of the ultrasound transducer probe 104 can intuitively keep track of their sonogram scans that they have performed during the examination of the human subject 102. On skilled in the arts appreciates that any sonogram scanning process may be used during examination of the human subject 102 because the orientation and location of the ultrasound transducer probe 104 with respect to the scan location on the human subject 102 is readily determinable. For example, sonogram scan can be aligned along a diagonal to the examined area of the human subject 102. Crisscrossing sonogram scans may be used for the examination, Even elliptical or circular scanning motions may be used during an examination. Such varying sonogram patterns, by the end of the examination process, will al result in generation of complete 3D image and/or 3D data for the examined area of the human subject 102.

The image processing algorithm module 120 receives the plurality of location indexed sonogram image information portions that are generated for each sonogram scan from the image registration module 118. The received location indexed sonogram image information portions for each sonogram scan are stored in a suitable memory medium (not shown) or in the database 124. In an example embodiment, each subsequently received location indexed sonogram image information portion is stored during the scanning process.

At the conclusion of the scanning process wherein the last location indexed sonogram image information portions generated from the last sonogram scan 144 is received, the location indexed sonogram image information for each individual sonogram scan is retrieved by the image processing algorithm module 120 for processing. The processing encompasses a plurality of processing steps.

An initial processing step performed by the image processing algorithm module 120 is to aggregate or combine the plurality of individual location indexed sonogram image information portions into composite sonogram image information. When the sonogram information and/or data is provided in discrete image files, individual image frames are selected for processing. When the sonogram information is provided as a continuous stream of data, the streaming echo return data is parsed using a suitable sampler algorithm into sonogram image portions. For example, one slice or frame may be taken from the streaming echo return data every 0.1 seconds and then saved for further processing. Any suitable sampling time may be used. Any suitable sampling application now known or later developed that transforms a continuous-time signal to a discrete time signal may be used by embodiments of the ultrasonagraphic system 100.

Since each of the individual location indexed sonogram image information portions are referenced to a reference location on the body of the human subject 102 (the reference location is determined from the location of the marker 130), each portion of the location indexed sonogram image information portions can be ordered by its particular location on the body of the human subject 102, and then may be combined with (or stitched together) with adjacent portions of the previously acquired location indexed sonogram image information portions and the subsequently acquired location indexed sonogram image information portions. For example, the second location indexed sonogram image information portion generated from the second sonogram scan 138 is combined with the adjacent previously generated first location sonogram image information portion (generated from the first sonogram scan 136). And, the second location indexed sonogram image information portion generated from the second sonogram scan 138 is combined with the adjacent previously generated third location sonogram image information portion (generated from the third sonogram scan 140). This combining of location indexed sonogram image information portions continues until all of the generated location indexed sonogram image information portions are combined into a single composite sonogram image information file or data. Any suitable methodology of combining together the location indexed sonogram image information portions, referred to in the arts as image stitching, that is now known or later developed, may be used by embodiments of the ultrasonagraphic system 100.

An alternative embodiment generates the composite sonogram image information by combining each received location indexed sonogram image information portions into the composite sonogram image information as they are received from the image registration module 118. Here, the composite sonogram image information is being generated in real time, or in near real time. As described herein, graphical presentation of the composite sonogram image information may be presented to the operator as each of the serial individual sonogram scans are performed. The "size" of the displayed graphical presentation of the composite sonogram image information will increase as each successive sonogram scan is being performed. Such immediate real time, or near real time, feedback may be particularly desirable to assist the operator in obtaining complete coverage of the portion of the body of the human subject 102 that is being examined. That is, if a portion of the body is missed in a scan, or the image information is unclear or corrupted, the operator may rescan the portion of the body of the human subject 102 that is of interest such that the subsequently acquired composite sonogram image information portions are integrated into the composite sonogram image information.

So long as the location of the marker 130 on the human subject 102 has not changed, additional sonogram scans may be performed by the operator after the last sonogram scan 144 has been performed. The subsequently acquired sonogram image information can then be correlated with previously acquired sonogram scan information. Thus, if a missed portion is later identified, and/or if additional image data for a particular region on the body is desired for clarity and/or improved resolution, the operator may re-scan that particular region of the body of the human subject 102. The subsequently acquired composite sonogram image information is then integrated into the previously generated composite sonogram image information. Because the ensuing sonogram scan is both time and location indexed, the subsequent scan does not need to be in parallel with the original sonogram scans. The subsequent sonographic scan(s) may be made along any direction of interest.

Once the composite sonogram image information has been generated, the composite sonogram image information may be stored into the database 124. The database 124 may be located locally, or may be remotely located. Once stored, the composite sonogram image information may be retrieved at a later time for processing.

Additionally, the image processing algorithm module 120 processes the composite sonogram image information into composite sonogram graphical information that can be used to render a 3D image and/or a 2D image. The composite sonogram graphical information may be optionally saved into the database 124.

Alternatively, or additionally, the generated composite sonogram graphical information may be communicated to the 3D/2D visualization module 122. The 3D/2D visualization module 122 processes (renders) the received composite sonogram graphical information into image information that can be communicated to the 3D/2D stereoscopic display 108, or to another suitable display device, for presentation to the operator or other individual. Any suitable image rendering process now known or later developed may be used by the 3D/2D visualization module 122 to generate presentable composite sonogram images. Alternatively, or additionally, the composite sonogram graphical information may be communicated to a remote display system 146 that is configured to render and present the composite sonogram images.

One skilled in the art appreciates that once the 3D composite sonogram graphical information has been generated from the composite sonogram image information, any suitable 3D image presentation algorithm may be used to display the body part of interest of the examined human subject 102. The graphical image, here the example spine of the human subject 102, may be rotated and/or oriented in any manner for view by the operator or another individual, such a s specialist doctor. Any suitable 3D processing algorithm now known or later developed may be used to present images generated from the composite sonogram graphical information.

Other analysis algorithms may be integrated into the image processing algorithm module 120, and/or work in conjunction with, the image processing algorithm module 120. For example, in the context of assessing degrees of scoliosis in the human subject 102, a spine modelling and measurement algorithm may be used to perform automatic measurement and analysis of the spine of the examined human subject 102.

Preferably, but not required, when the ultrasonagraphic system 100 is used to examine bone structure of the human subject 102, the image processing algorithm module 120 includes a filtering algorithm that filters non-bone type sonogram echo information out from the composite sonogram image information (or the plurality of location indexed sonogram image information). Here, background information in the detected sonic echo information is suppressed so that only echoes from the bone structure of the human subject 102 is retained for analysis.

Alternatively, or additionally, other filtering algorithms may be used to identify and isolate other tissues or structures of interest in the examined human subject 102. For example, if images of a particular soft tissue in the human subject 102 is of interest, echo information generated by nearby bones may be suppressed by a filtering algorithm such that the composite sonogram image information is filtered to produce 3D and/or 2D graphical images of the tissue of interest (organs of interest).

Use of ultrasound transducer probes 104 has not provided satisfactory because the sonogram images were too noisy so that a high degree of discrimination of particular organs and/or anatomy of interest simply was not possible. The novel approach of applying a particular filter to the sonogram information prior to attempting to construct the 3D image and/or 3D data now enables embodiments of the ultrasonagraphic system 100 to discern particular organs of interest. Here, the example application described an examination of the spine of the original human subject 102. The applied filter is configured to filter out sonogram information that is unrelated to the spine bones of interest.

Preferably, but not required, an artificial intelligence (AI) algorithm may be used by the image processing algorithm module 120 to enhance the quality and/or reliability of the generated composite sonogram image information. Convolutional neural networks (CNNs) may be used for image processing by embodiments of the ultrasonagraphic system 100. The AI algorithm learns to further process the received filtered sonogram information to provide an improved highlight of the organ or anatomy of interest that is being examined. For example, but not limited to, the AI system may learn to identify particular anatomical landmarks of interest. Any suitable AI systems and/or neural networks now known or later developed may be used by the various embodiments of the ultrasonagraphic system 100.

For example, if particular anatomical landmarks on the spine of the human subject 102 are of interest, information identifying such landmarks may be provided to the image processing algorithm module 120, and in particular to the AI algorithm. Over time, as a greater number of like landmarks are identified by the AI algorithm in other composite sonogram image information acquired from other human subjects 102, or even later acquired sonogram information from the original human subject 102, the AI algorithm may learn to identify the anatomical landmarks of interest.

For example, to assess the position and orientation of the spine, it is currently necessary to interact with the 3D reconstruction when generating the 3D image and/or 3D model data. This process of manually adding points can take time and can be less than perfect. To speed of the process, embodiments of the ultrasonagraphic system 100 trains an AI model that can assess the 3D reconstruction volume in its entirety and assign label to an area by coloring it or other methods. The generated 3D image and/or 3D model data may be marked by hand and then the AI is trained to identify the landmark in a similar pattern on a different 3D volume. The landmarks that are detected can be identified and analyzed after the volume is collected or live while the 3D volume is being made in real-time.

In a preferred embodiment, the AI algorithm may optionally be configured to compute and/or acquire measurement information pertaining to a particular anatomical structure of interest. In the case of an examination of the spine of the human subject 102, an example embodiment assess orientation and/or location of particular spine bones. That is, a degree of curvature, rotation and/or tilt between individual spine bones (vertebrae) can be automatically determined. Measurements of the angular displacement and/or the location displacement of the spine bones can be determined. Embodiments of the ultrasonagraphic system 100 may have the AI algorithm learn to determine any anatomical measurement of interest for any organ and/or anatomy of interest that is being examined.

Further, when the graphical presentation of the composite sonogram image information is made on the 3D or 2D display 108, the AI algorithm may modify the graphical image to generate an annotated image that presents one or more graphical artifacts to highlight and/or present indicating information to the operator or other interested person viewing the presented graphical image. In the context of the examination of the spine of the human subject 102, the generated graphical artifacts can be used to provide a visual indication of the determined measurements of the angular displacement and/or the location displacement of the spine bones.

Figure 2:
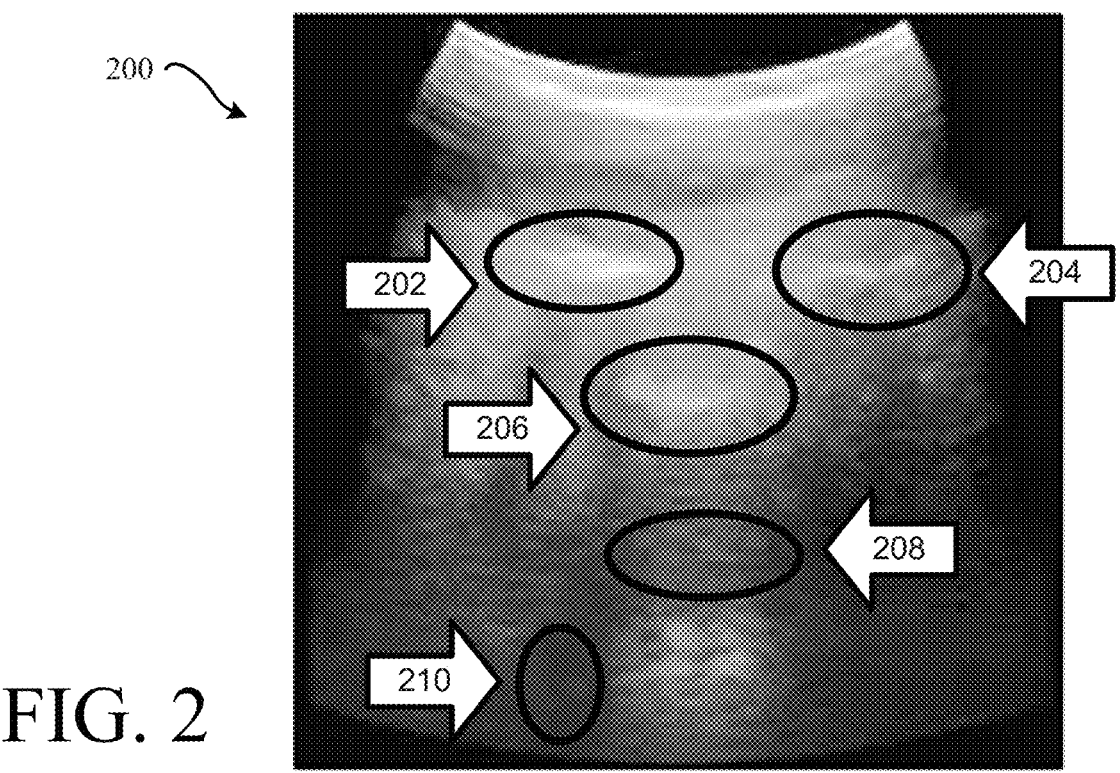
FIG. 2 is a graphical image of the spine of a test human subject that has been examined using an embodiment of the ultrasonagraphic system.

FIG. 2 is a graphical image 200 of the spine of a test human subject 102 that has been examined using an embodiment of the ultrasonagraphic system 100. The image 200 presents a graphical image of a portion of the spine of an examined human subject 102. The indicated region 202 informs the operator or other interested party that the very light areas of the image portion 202 is showing a sonographic image a particular bone in the spine of the examined human subject 102. The indicated region 204 similarly indicates that the very light areas of the image portion 204 is showing a sonographic image of a different bone in the spine of the examined human subject 102. The indicated region 206 is also a very light area, but due to a lighter region 208 region 206 is not characteristic of bone. Region 206 is likely a ligament or muscle surface connecting bones corresponding to regions 202 and 206. The indicated regions like 210 similarly indicate that the darker shaded areas of the image portion are showing a sonographic image corresponding to regions of bone surface under the ultrasound transducer probe 104. The bone surfaces reflect most of the ultrasound, causing darker areas under the spine of the examined human subject 102.

Figure 3:
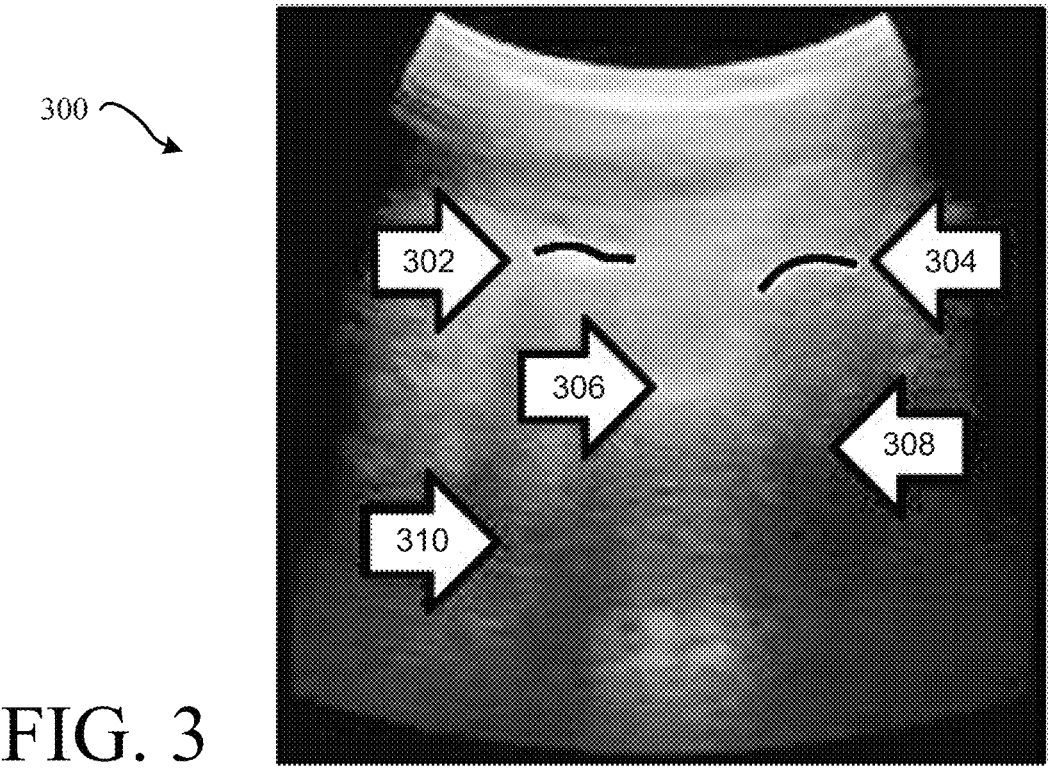
FIG. 3 is a graphical image of the spine of a test human subject after the AI algorithm of the image processing algorithm module has analyzed particular spine bones and has added a graphical artifact overlaid over the image of the spine bone.

FIG. 3 is a graphical image 300 of the spine of a test human subject 102 after the AI algorithm of the image processing algorithm module 120 has analyzed particular spine bones and has added one or more graphical artifacts overlaid over the image of the spine of the human subject 102. The graphical artifacts impart information to the operator or other interested party regarding the state or condition of the associated spine. For example, a single presented image of the spine of the human subject 102 may be measured to ascertain spinal curvatures in all directions and planes. Additionally, or alternatively, a selected plane of a 3D image and/or 3D data may be used to generate a 2D image and/or 2D data along the plane of interest.

The absence of graphical artifacts to the regions 306, 308 and 310 (which correspond to the regions 206, 208 and 210, respectively, of FIG. 2) indicates that these regions of the examined human subject 102 have no information of particular interest, and/or were associated with other tissues that were not under examination. Accordingly, no graphical artifacts were generated for these regions 306, 208 or 310.

Figure 5:
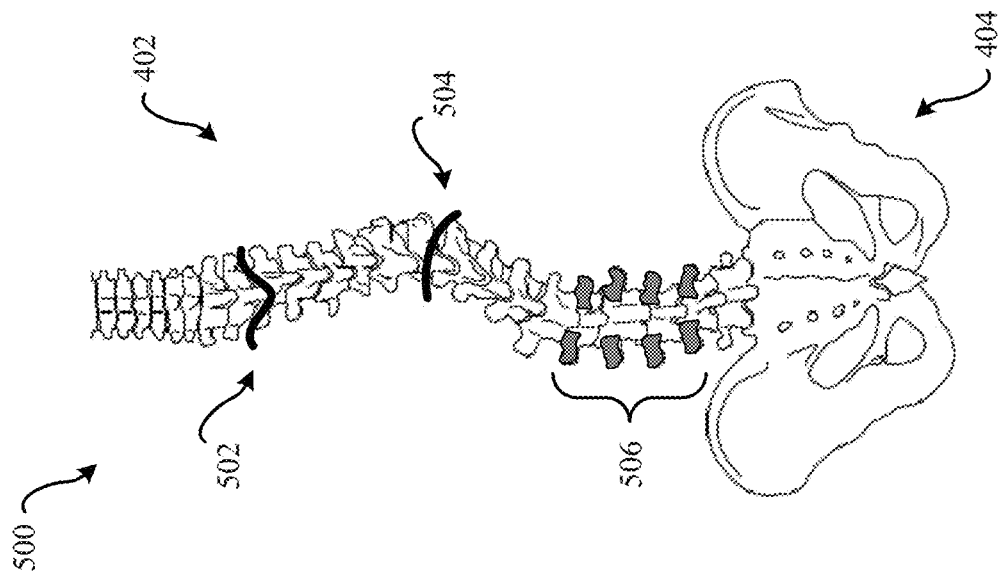
FIG. 5 is a conceptual diagram of a 3D or 2D image generated from the composite sonogram graphical information presenting an image of the spine and pelvic bone of the human subject.
Figure 4:
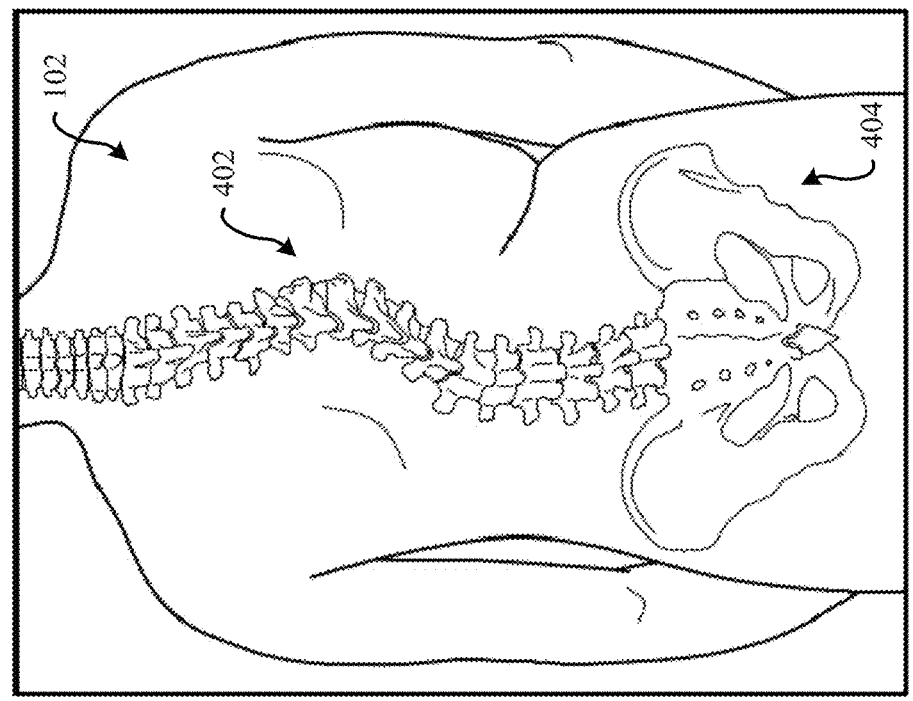
FIG. 4 is a conceptual diagram of the human subject showing their spine and their pelvic bone.

FIG. 4 is a conceptual diagram 400 of the human subject 102 showing their spine 402 and their pelvic bone 404. FIG. 5 is a conceptual diagram 500 of a 3D or 2D image generated from the composite sonogram graphical information presenting an image of the spine 402 and pelvic bone 404 of the human subject 102. The image 500 illustrates a first graphical artifact 502 (corresponding to the graphical artifact 302 of FIG. 3) and a second graphical artifact 504 (corresponding to the graphical artifact 304 of FIG. 3). There, the AI algorithm of the image processing algorithm module 120 has presented useful diagnostic information to the viewing operator or other interested party.

In some embodiments, graphical artifacts may be generated to highlight particular anatomical features of interest to aid the assessment of the condition of the examined human subject 102. For example, a plurality of graphical artifacts 506 highlighting the outward protruding portions of each spine bone (bumps) can be generated and then overlaid over the generated image of the spine. Various colors, shading and/or illumination intensities may be used in the presented graphical artifacts 506 to aid the examiner in assessing the condition of the spine of the human subject 102. In this simplified conceptual example, the graphical artifacts 506 were generated and presented for only four spine bones. However, the graphical artifacts 506 may be generated and presented for all of the spine bones, or for selected spine bones of interest. Further, with an interactive display 108 and a suitable graphical user interface (GUI), the examiner may interactively select and/or manipulate any presented graphical artifacts 502, 504, and/or 506.

The 3D or 2D image of the spine is generated by the image processing algorithm module 120 during the further processing of the composite sonogram image information. Here, after extensive filtering, image information or data identifying the particular bones in the spine of the human subject 102 are identified with a high degree of discrimination. Further, the AI algorithm may have learned to identify particular bones of the spine of the human subject 102. The AI may access suitable skins (image data that graphically depict a more realistic image of a bone) for each particular bone in the spine of the human subject 102, and use the accessed skins to create a more realistic graphical representation of the spine.

In some embodiments, a corresponding ideal structure image may be accessed from a database and overlaid over the top of, or presented adjacent to, the image generated based on the sonogram examination. For example, image data of an ideal spine may be accessed. The image data of the ideal spine may then be scaled to correspond to the image of the spine of the human subject 102. Then the overlaid or adjacent image of the ideal spine can be visually compared with the image of the spine of the examined human subject 102. The comparison may be performed using 3D or 2D images.

Figure 6:
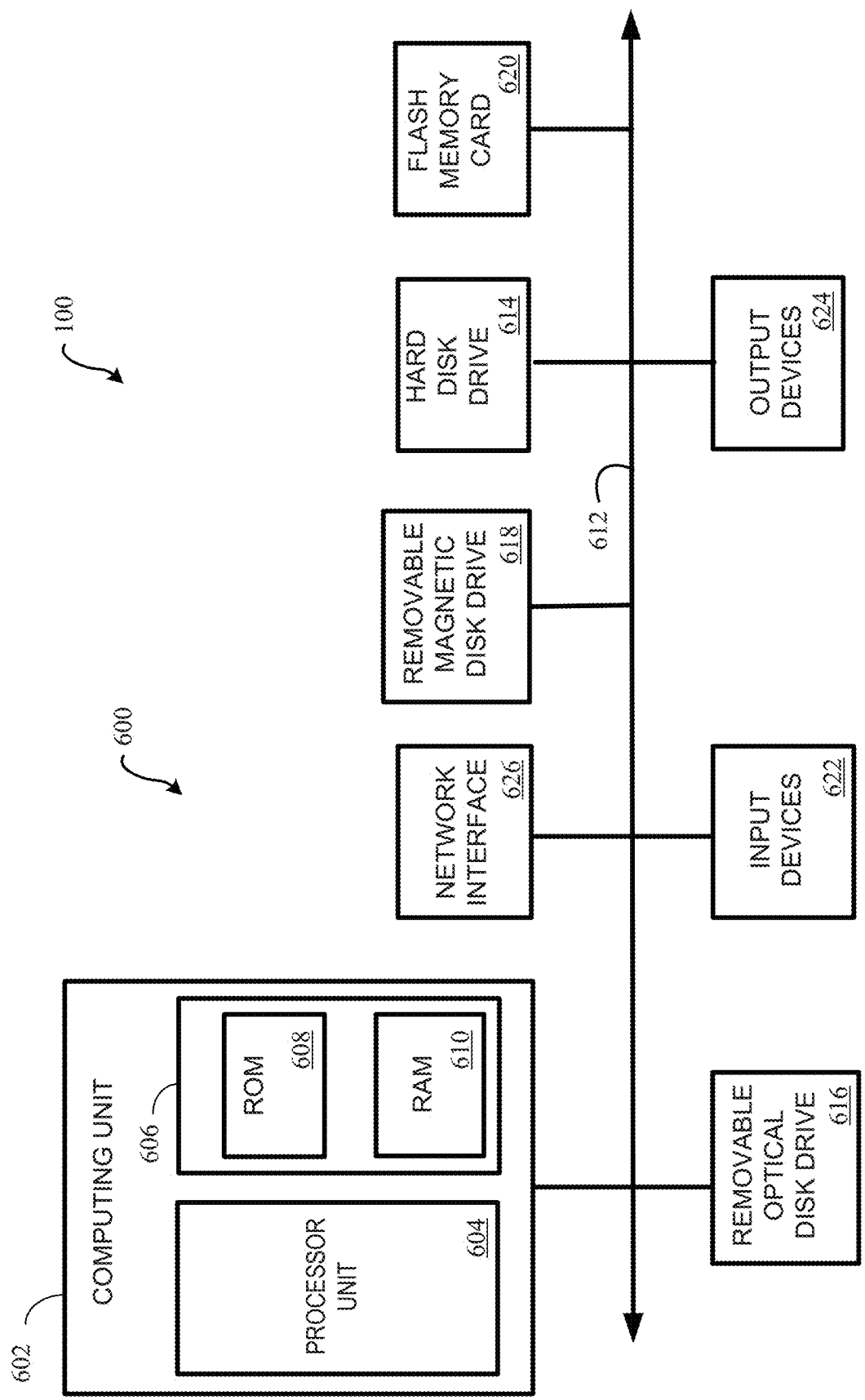
FIG. 6 is a block diagram of a programmable computing device suitable for use as part of the image processing system embodied with an ultrasonagraphic system.

FIG. 6 is a block diagram of a programmable computing device suitable for use as part of the image processing system 600 embodied with an ultrasonagraphic system 100. While the following paragraphs describe one suitable example of an image processing system, one skilled in the art will understand that many different examples are contemplated. For example, image processing system 600 could include an embedded software system, a standalone personal computer, and/or a networked computer system.

From the disclosure of the ultrasonagraphic system 100, those skilled in the art will recognize that various examples of the image processing system 600 may be implemented using electronic circuitry configured to perform one or more functions. For example, with some embodiments of the invention, the image processing system may be implemented using one or more application-specific integrated circuits (ASICs). In some examples, however, components of various examples of the invention will be implemented using a programmable computing device executing firmware or software instructions, or by some combination of purpose-specific electronic circuitry and firmware or software instructions executing on a programmable computing device.

Accordingly, FIG. 6 shows one illustrative example of an image processing system 600, a computer, that can be used to implement various embodiments of the invention. As seen in this figure, the example image processing system 600 has a computing unit 602. Computing unit 602 typically includes a processing unit 604 and a system memory 606. Processing unit 604 may be any type of processing device for executing software instructions, but will conventionally be a microprocessor device. System memory 606 may include both a read-only memory (ROM) 608 and a random access memory (RAM) 610. As will be appreciated by those of ordinary skill in the art, both read-only memory (ROM) 608 and random access memory (RAM) 610 may store software instructions to be executed by processing unit 604.

Processing unit 604 and system memory 606 are connected, either directly or indirectly, through a bus 612 or alternate communication structure to one or more peripheral devices. For example, processing unit 604 or system memory 606 may be directly or indirectly connected to additional memory storage, such as a hard disk drive 614, a removable optical disk drive 616, a removable magnetic disk drive 618, and a flash memory card 620. Processing unit 604 and system memory 606 also may be directly or indirectly connected to one or more input devices 622 and one or more output devices 624. Input devices 622 may include, for example, a keyboard, touch screen, a remote control pad, a pointing device (such as a mouse, touchpad, stylus, trackball, or joystick), a scanner, a camera or a microphone. Output devices 624 may include, for example, a monitor display, an integrated display, television, printer, stereo, or speakers.

Still further, computing unit 602 will be directly or indirectly connected to one or more network interfaces 626 for communicating with a network. This type of network interface 626, also sometimes referred to as a network adapter or network interface card (NIC), translates data and control signals from computing unit 602 into network messages according to one or more communication protocols, such as the Transmission Control Protocol (TCP), the Internet Protocol (IP), and the User Datagram Protocol (UDP). These protocols are well known in the art, and thus will not be discussed here in more detail. An interface 626 may employ any suitable connection agent for connecting to a network, including, for example, a wireless transceiver, a power line adapter, a modem, or an Ethernet connection.

It should be appreciated that, in addition to the input, output and storage peripheral devices specifically listed above, the computing device may be connected to a variety of other peripheral devices, including some that may perform input, output and storage functions, or some combination thereof. For example, the computer 101 will often be connected to the 3D ultrasound processor and transducer system. In addition to a 3D ultrasound unit, computer 101 may be connected to or otherwise include one or more other peripheral devices, such as a telephone, facsimile machine, router or the like.

The telephone may be, for example, a wireless "smart phone," such as those featuring the Android or iOS operating systems. As known in the art, this type of telephone communicates through a wireless network using radio frequency transmissions. In addition to simple communication functionality, a "smart phone" may also provide a user with one or more data management functions, such as sending, receiving and viewing electronic messages (e.g., electronic mail messages, SMS text messages, etc.), recording or playing back sound files, recording or playing back image files (e.g., still picture or moving video image files), viewing and editing files with text (e.g., Microsoft Word or Excel files, or Adobe Acrobat files), etc. Because of the data management capability of this type of telephone, a user may connect the telephone with computing unit 602 so that their data maintained may be synchronized.

Of course, still other peripheral devices may be included with or otherwise connected to a computing unit 602 of the type illustrated in FIG. 2, as is well known in the art. In some cases, a peripheral device may be permanently or semi-permanently connected to computing unit 602. For example, with many computers, computing unit 602, hard disk drive 614, removable optical disk drive 616 and a display are semi-permanently encased in a single housing.

Still other peripheral devices may be removably connected to computing unit 602, however. Computing unit 602 may include, for example, one or more communication ports through which a peripheral device can be connected to computing unit 602 (either directly or indirectly through bus 612). These communication ports may thus include a parallel bus port or a serial bus port, such as a serial bus port using the Universal Serial Bus (USB) standard or the IEEE 1394 High Speed Serial Bus standard (e.g., a Firewire port). Alternately or additionally, computer 101 may include a wireless data "port," such as a Bluetooth® interface, a Wi-Fi interface, an infrared data port, or the like.

It should be appreciated that a computing device employed according to various examples of the invention may include more components other than, or in addition to, the computing unit 602 illustrated in FIG. 6. Further, fewer components than computing unit 602, or a different combination of components than computing unit 602, may be used by alternative embodiments. Some implementations of the invention, for example, may employ one or more computing devices that are intended to have a very specific functionality, such as a server computer. These computing devices may thus omit unnecessary peripherals, such as the network interface 626, removable optical disk drive 616, printers, scanners, external hard drives, etc. Some implementations of the invention may alternately or additionally employ computing devices that are intended to be capable of a wide variety of functions, such as a desktop or laptop personal computer. These computing devices may have any combination of peripheral devices or additional components as desired.

Further, in another practice example, the ultrasonagraphic system 100 can be used to recall previously generated images and/or data of the spine of the human subject 102 at a later time. As noted herein, the previous images and/or data can be stored in the computer system of the ultrasonagraphic system 100 and/or a local or remote database. The ultrasonagraphic system 100 then matches current 3D images of the spine of the human subject 102 with previously acquired images. In this example application, the compared images can be used to assist the operator in assessment spinal health and/or treatment effectiveness for the spine of the human subject 102.

Embodiments of the ultrasonagraphic system 100, in addition to obtaining image information and generated 3D or 2D model information or data for scanned tissues, bones or organs of a human subject 102, may be suited for obtaining sonogram information from other animals, such as, but not limited to pets, livestock, zoo animals, or the like. Embodiments of the ultrasonagraphic system 100 may also be used to obtain sonogram information from plants or other inanimate objects. For example, ancient artifacts or relics that are suitable for scanning using an ultrasound transducer probe could be scanned using an embodiment of the ultrasonagraphic system 100. Further, sonograph scans are often used to scan prenatal infants while in their mother's womb. Embodiments of the ultrasonagraphic system 100 could also be used to scan these infants.

One skilled in the arts appreciates that embodiments of the ultrasonagraphic system 100 may also be configured to detect, discriminate, identify and then present other non-biological objects that are within the human subject 102. For example, metallic or polymer pins, screws, braces or the like may have been implanted into the human subject 102 during prior surgical procedures. Such objects can be identified and then added into the generated 3D or 2D model information or data. Further, since the 3D or 2D model information or data can be generated in real time, or in near real time, surgical instruments currently used during a procedure that the human subject 102 is undergoing can be identified. Here, the ultrasonagraphic system 100 can be used to concurrently detect such surgical instruments along with the organs or tissue of interest.

One skilled in the art appreciates that the ultrasonagraphic processor system 106 does to need to be local to or in proximity to the ultrasound transducer probe 104 during examination of the human subject 102. Here, the image capture device 114 needs to be local to the human subject 102 during the sonogram scanning process so as to capture images of the targets 130, 132 during the examination of the human subject 102. Such embodiments may be configured to be remotely located from the ultrasound transducer probe 104 and the image capture device(s) 114. The ultrasonagraphic processor system 106 receives the ultrasound information and the camera images via a suitable communication system that communicatively couples the ultrasonagraphic processor system 106 with the ultrasound transducer probe 104 and the image capture device(s) 114. Further, such embodiments may be configured to receive information from multiple ultrasound transducer probes 104 and image capture device(s) 114 so that multiple human subjects 102 may be remotely and/or concurrently examined. Further, the generated 3D/2D image and/or 3D/2D model data may be communicated back to the examination site for display on a display device that is located in at the examination site.

Figure 7:
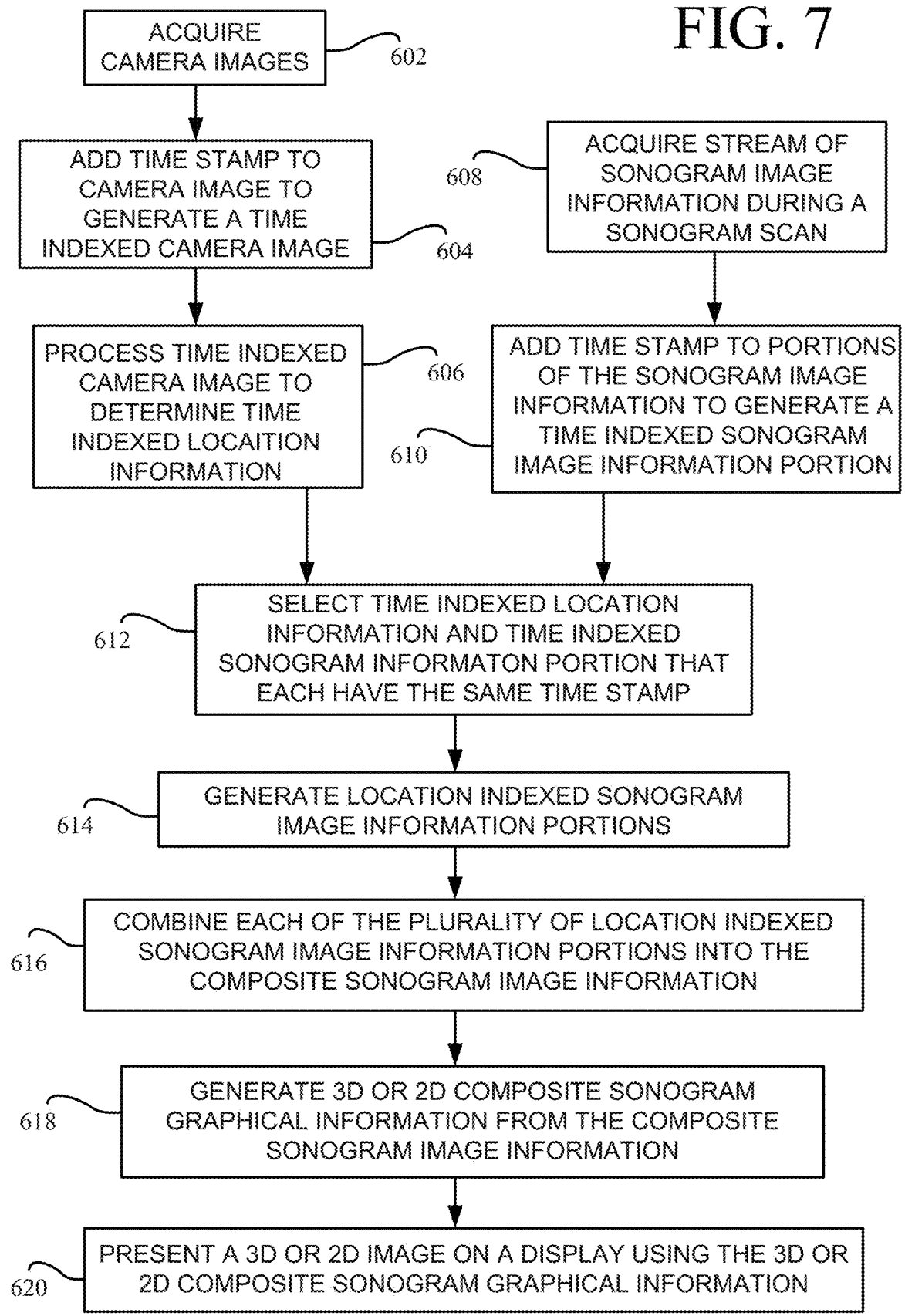
FIG. 7 is a flow chart depicting a process used by an example embodiment of the ultrasonagraphic system.

FIG. 7 is a flow chart depicting a process used by an example embodiment of the ultrasonagraphic system 100. Camera images and a stream of sonogram image information are acquired during a sonogram scan (602). A time stamp is added to the camera image to generate a time indexed camera image (604). The same, or substantially the same, time stamp is added to the corresponding portion of the sonogram image information to generate a time indexed sonogram image information portion.

Each time indexed camera image is processed to determine a corresponding time indexed location information that identifies the particular portion of the human subject 102 that was being scanned during the time of the time stamp (606).

Concurrently, a stream of sonogram image information is acquired during a plurality of sonogram scans (608). A time stamp is added to portions of the sonogram image information to generate a time indexed sonogram image information portion (610).

Then, for a selected time (612), the time indexed location information for the selected time is combined with the time indexed sonogram image information portion (that was acquired at the same time of the time stamp) to generate a location indexed sonogram image information portion for that particular portion of the sonogram information (614).

Then, each of the plurality of location indexed sonogram image information portions are combined to generate the composite sonogram image information (616). The composite sonogram image information is then used to generate 3D or 2D composite sonogram graphical information (618) which may be used to render 3D or 2D images on a display (620).

Alternative embodiments may employ other methods and apparatus of tracking the position and orientation of the ultrasound transducer probe 104 used by the ultrasonagraphic system 100 to identify tissues (organs) and bones of the human subject 102 (FIG. 1).

Figure 8:
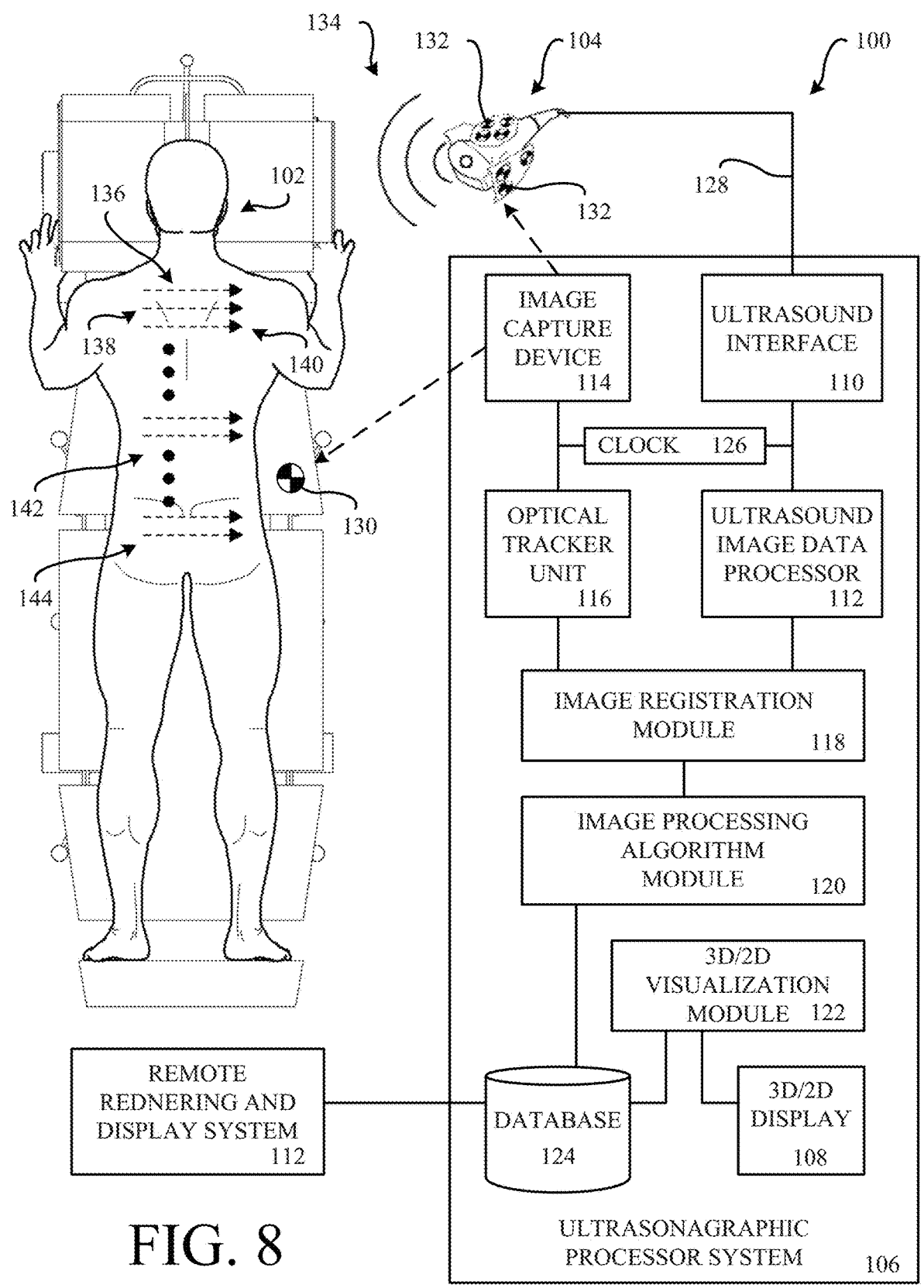
FIG. 8 is a schematic view of an alternative embodiment of the ultrasonagraphic system for examining a human subject where the optical target is not located on the human subject.

FIG. 8 is a schematic view of an alternative embodiment of the ultrasonagraphic system 100 for examining a human subject 102 where the optical target 130 is not located proximate to, but not on, the human subject 102. In this non-limiting example embodiment, the optical target 130 is placed on a stationary object (rather than the human subject 102). Alternatively, a stationary object proximate to the human subject 102 that is identifiable in a captured image may be used instead of the optical target 130.

Figure 9:
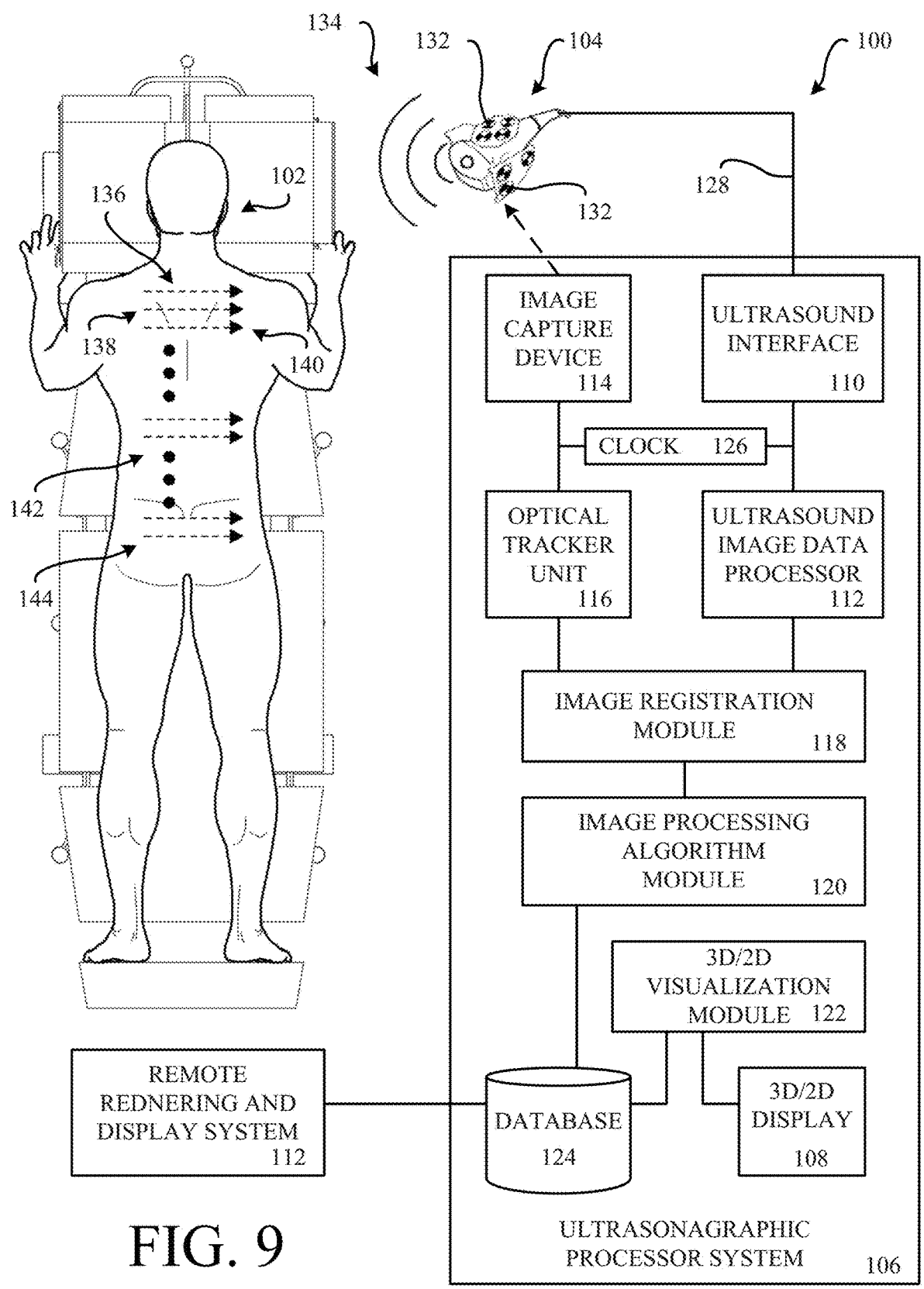
FIG. 9 is a schematic view of an alternative embodiment of the ultrasonagraphic system for examining a human subject where the optical target is not used.

FIG. 9 is a schematic view of an alternative embodiment of the ultrasonagraphic system 100 for examining a human subject 102 where the optical target 130 is not used. Here, only the position and orientation of the ultrasound transducer probe 104 is tracked during the series of ultrasonic scans.

Using the embodiments illustrated in FIGS. 8 and 9, the human subject 102 remains still, or at least substantially still, during the scanning process. The ultrasonagraphic system 100 receives the sonogram image information from the ultrasound transducer probe 104 during a series of ultrasonic scans. The spatial relationship between the scanned tissue of interest and the acquired sonogram image information is determinable for generation of the 3D image and/or 3D model data.

With these embodiments, the practitioner may view the generated 3D image and/or 3D model data on the display 108. Based on the experience of the practitioner, and the approximate known area of the human subject 102 that was scanned, the practitioner can make an intuitive judgement to identify what tissue or bone structure is being shown in the viewed 3D image and/or 3D model data.

Figure 10:
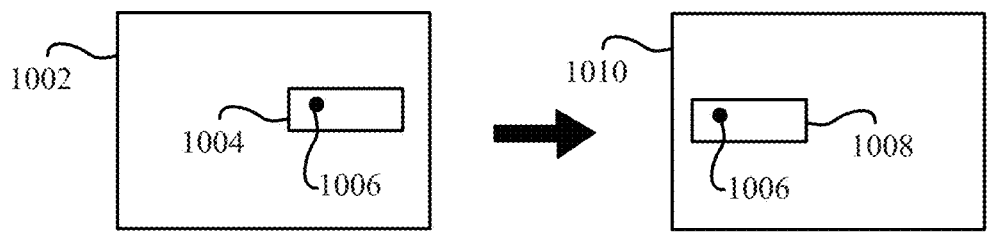
FIG. 10 illustrates two image frames of sonogram image information.

An alternative embodiment employs a multi-kernel block matching algorithm. FIG. 10 illustrates two image frames of sonogram image information. A block matching algorithm divides a first selected image frame 1002 into macroblocks, wherein a first macroblock 1004 is selected. Preferably, the selected first macroblock 1002 includes a readily identifiable graphical artifact 1006.

A macroblock 1008 corresponding to the first macroblock 1004 is identified in the second selected image frame 1010. The corresponding macroblock 1008 is identifiable since it also includes the graphical artifact 1006.

The two macroblocks 1004, 1008 are compared to define a distance of travel corresponding to motion of the ultrasound transducer probe 104 during the ultrasonic scan. Time information that identifies the time that the first and second sonogram image information was acquired can be compared to determine a time of capture between the two macroblocks 1004, 1008. A vector is then determined that models the movement of a macroblock from one location to another location. This determined movement of the macroblocks 1004, 1008 constitutes a motion estimation of the ultrasound transducer probe 104.

As the practitioner conducts a series of ultrasonic scans over the human subject 102, the graphical artifact 1006 may be identified in the images of a subsequent ultrasonic scan. Based on the location of the graphical artifact 1006 in the sonogram image information of the subsequent scan, the location relationship between the sonogram image information of the preceding ultrasonic scan and the subsequent ultrasonic scan can be computed.

As the ultrasonic scanning process continues, at some juncture the graphical artifact 1006 may not be present in the sonogram image information acquired during subsequent ultrasonic scans. However, a different graphical artifact may have been identified in at least one the subsequent ultrasonic scan that may be used to compute the location relationship between ultrasonic scans. So long as there is at least one sonogram image information frame that includes the two identified graphical artifacts, the location relationship between the sonogram image information from all of the ultrasonic scans can be computed.

Figure 11:
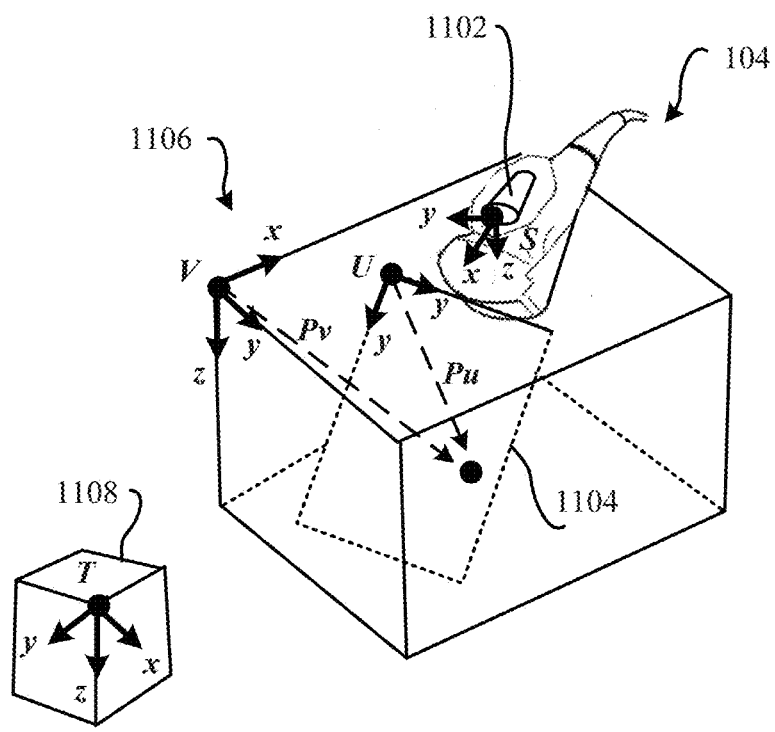
FIG. 11 illustrates an alternative embodiment of the ultrasonagraphic system that employs an electromagnetic sensor.

FIG. 11 illustrates an alternative embodiment of the ultrasonagraphic system 100 that employs an electromagnetic (E/M) sensor 1102. The E/M sensor 1102 is placed on the head of the ultrasound transducer probe 104 and optionally on the patient (not shown) to track to positions relative to each other. Alternatively, the patient can be kept still and just use the ultrasound tracking E/M sensor 102 relative to the room or the space in which it is placed. Accordingly, the ultrasound frame 1104 is captured and recorded in 3D space 1106. An electromagnetic transducer 1108, at a known reference location and orientation, emits an electromagnetic field that is detectable by the electromagnetic sensor 1102. The detected electromagnetic field is used to determine the location and orientation of the ultrasound transducer probe 104.

Figure 12:
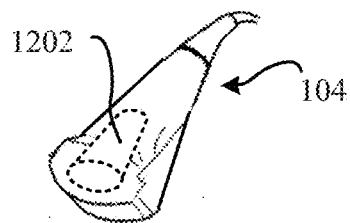
FIG. 12 illustrates an alternative embodiment that employs an internal moveable ultrasonic transmitter within the ultrasound transducer probe.
Figure 13A:
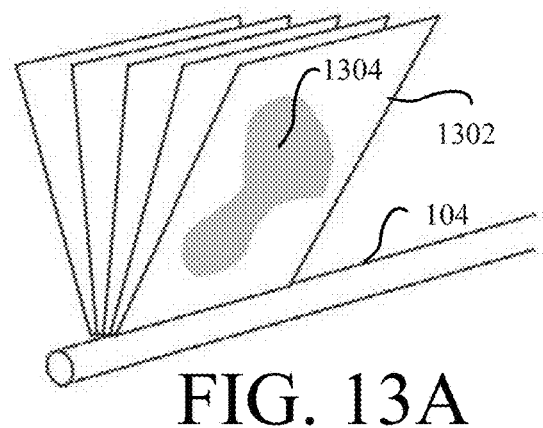
FIG. 13a illustrates that the moveable ultrasonic transmitter moves in an arc pattern by some predefined angle between ultrasound scans.
Figure 13B:
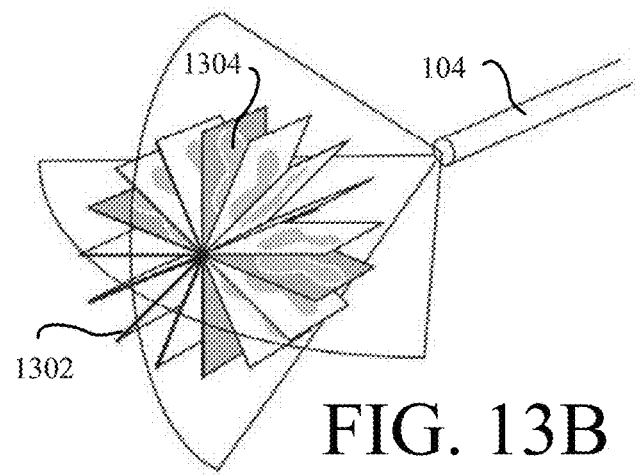
FIG. 13b illustrates that the moveable ultrasonic transmitter rotates 180 degrees by some predefined angle between ultrasound scans.
Figure 13C:
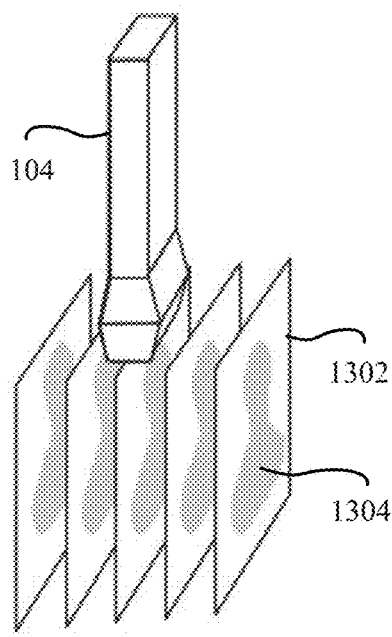
FIG. 13c illustrates that the moveable ultrasonic transmitter moves laterally by some lateral distance between ultrasound scans.
Figure 13D:
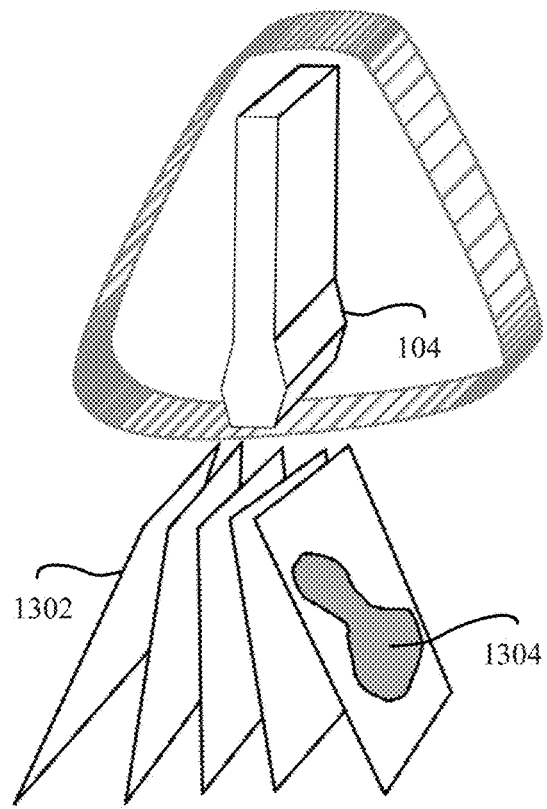
FIG. 13d illustrates that the moveable ultrasonic transmitter moves by some predefined angular displacement between ultrasound scans.

FIG. 12 illustrates an alternative embodiment that employs an internal moveable ultrasonic transmitter 1202 within the ultrasound transducer probe 104. The automatically moving ultrasonic transmitter 1202 sweeps in different directions to generate 3D image and/or 3D model data based on the sonogram image information acquired as the ultrasonic transmitter 1202 sweeps across the human subject 102 (FIG. 1). FIGS. 13a-13d illustrate various sweep patterns that a moveable ultrasonic transmitter 1202 might make. In FIG. 13a the moveable ultrasonic transmitter 1202 moves in an arc pattern by some predefined angle between ultrasound scans. In FIG. 13b the moveable ultrasonic transmitter 1202 rotates 180 degrees by some predefined angle between ultrasound scans. In FIG. 13c the moveable ultrasonic transmitter 1202 moves laterally by some lateral distance between ultrasound scans. FIG. 13d the moveable ultrasonic transmitter 1202 moves by some predefined angular displacement between ultrasound scans.

With such embodiments, the AI algorithm can be used to improve accuracy in the generation of 3D image and/or 3D model data from a series of sonogram image information 1302 acquired as the transmitter 1202 automatically moves in proximity to the scanned tissue of interest 1304. Further, if the ultrasound transducer probe 104 is moved to a different location on the human subject 102, MEMs devices may optionally be used to determine location of the ultrasound transducer probe 104 for a series of scans on the human subject 102.

In the field of cardiology and medical imaging, speckle tracking echocardio-graphy (STE) is an echocardiographic imaging technique. STE analyzes the motion of tissues in the heart or other organs by using the naturally occurring speckle pattern in the myocardium (or in the motion of blood) when imaged by ultrasound using the ultrasound transducer probe 104. The STE method of documentation of myocardial motion is a noninvasive method of definition for both vectors and velocity. Here, the series of sonogram image information captured along one scan plane, followed by a series of sonogram image information captured along the next scan plane can be used to construct time variant generate 3D image and/or 3D model data. Here, the practitioner will be able to view images that corresponds to a 3D movie.

In some embodiments, two or more of the above-described features may be used together to improve accuracy of the generated 3D image and/or 3D model data.

It should be emphasized that the above-described embodiments of the ultrasonagraphic system 100 are merely possible examples of implementations of the invention. Many variations and modifications may be made to the above-described embodiments. All such modifications and variations are intended to be included herein within the scope of this disclosure and protected by the following claims.

Furthermore, the disclosure above encompasses multiple distinct inventions with independent utility. While each of these inventions has been disclosed in a particular form, the specific embodiments disclosed and illustrated above are not to be considered in a limiting sense as numerous variations are possible. The subject matter of the inventions includes all novel and non-obvious combinations and subcombinations of the various elements, features, functions and/or properties disclosed above and inherent to those skilled in the art pertaining to such inventions. Where the disclosure or subsequently filed claims recite "a" element, "a first" element, or any such equivalent term, the disclosure or claims should be understood to incorporate one or more such elements, neither requiring nor excluding two or more such elements.

Applicant(s) reserves the right to submit claims directed to combinations and subcombinations of the disclosed inventions that are believed to be novel and non-obvious. Inventions embodied in other combinations and subcombinations of features, functions, elements and/or properties may be claimed through amendment of those claims or presentation of new claims in the present application or in a related application. Such amended or new claims, whether they are directed to the same invention or a different invention and whether they are different, broader, narrower or equal in scope to the original claims, are to be considered within the subject matter of the inventions described herein.

Therefore, having thus described the invention, at least the following is claimed:

1. An ultrasonagraphic three dimensional (3D) model generation system, comprising:
   an ultrasound image data processor communicatively coupled to an ultrasound transducer probe that is configured to acquire sonogram image information from a serial plurality of ultrasound scans of a human subject, wherein the ultrasound transducer probe generates the sonogram image information during each one of the plurality of ultrasound scans, wherein the ultrasound transducer probe receives the sonogram image information from the ultrasound transducer probe, and wherein the ultrasound image data processor generates a plurality of time indexed sonogram image information portions that each include the sonogram image information and a first time that corresponds to a time of acquisition of the sonogram image information;

at least one image capture device that captures a time sequenced series of camera images that include both the human subject and the ultrasound transducer probe, wherein at least one first optical target that is located on the human subject is visible in each one of the series of captured camera images, and wherein at least one second optical target that is located on the ultrasound transducer probe is visible in each one of the series captured camera images;

an optical tracker unit communicatively coupled to the at least one image capture device, wherein the optical tracker unit receives each one of the series of camera images from the at least one image capture device, wherein each one of the series of camera images includes a time that indicates a time of acquisition of the camera image by the at least one image capture device;

wherein the optical tracker unit determines a location of the at least one first target on the human subject and a location of the at least one second target on the ultrasound transducer probe, wherein the optical tracker unit determines time indexed location information for each camera image based on the determined locations of the first optical target and the second optical target, wherein the time indexed location information identifies a portion of the human subject that is being scanned by the ultrasound transducer probe based on the determined location of the at least one optical target on the human subject and the at least one second optical target on the ultrasound transducer probe, and wherein the time indexed location information includes the second time;

an image registration module that is communicatively coupled to the ultrasound image data processor and the at least one image capture device, wherein the image registration module selects, for each time indexed sonogram image information portion, the time indexed location information that has the same second time, and wherein the image registration module generates a plurality of location indexed sonogram information portions based on the each one of the time indexed sonogram image information portions and the corresponding time indexed location information; and an image processing algorithm module that is communicatively coupled to the image registration module, wherein the image processing algorithm module receives the plurality of location indexed sonogram image information portions from the image registration module, and wherein the image processing algorithm module combines the received plurality of location indexed sonogram image information portions to generate a composite sonogram image information, wherein a 3D model is generated based on the generated composite sonogram image information.

2. The ultrasonagraphic 3D model generation system of claim 1, wherein the image processing algorithm module generates 3D composite sonogram graphical information based on the generated composite sonogram image information.

3. The ultrasonagraphic 3D model generation system of claim 2, further comprising:
a 3D visualization module that generates an image based on the 3D composite sonogram graphical information, wherein the image is presentable on a display.

4. The ultrasonagraphic 3D model generation system of claim 1, further comprising:
a 3D visualization module that generates an image based on the 3D model,
wherein the image is presentable on a display.

5. The ultrasonagraphic 3D model generation system of claim 1, wherein the image processing algorithm module generates 3D composite sonogram graphical information based on the generated composite sonogram image information model, and wherein the generated 3D composite sonogram graphical information is defined as a collection of points in a 3D space corresponding to a surface of an organ or interest.

6. The ultrasonagraphic 3D model generation system of claim 5, wherein the collection of points in the 3D space is a point cloud of geometric samples on the surface of the organ of interest.

7. The ultrasonagraphic 3D model generation system of claim 1, further comprising:
at least one clock,
wherein the at least one clock provides the time of acquisition of the ultrasound information by the ultrasound transducer probe,
wherein the at least one clock provides the time of acquisition of the camera image that is captured by the at least one image capture device.

8. A method of generating three dimensional (3D) model data based on a serial plurality of ultrasound scans of a human subject that are acquired using an ultrasonagraphic system, comprising:
generating a plurality of time indexed sonogram image information portions that each include sonogram image information from a portion of the ultrasound scan and a first time that corresponds to a time of acquisition of the sonogram image information portion;
capturing a time sequenced series of camera images that include both the human subject and the ultrasound transducer probe using at least one image capture device, wherein each one of the series of camera images includes a second time that indicates a time of acquisition of the camera image by the at least one image capture device;
determining time indexed location information for each camera image,
wherein the time indexed location information identifies a location of a portion of the human subject that is being scanned by the ultrasound transducer probe, and
wherein the time indexed location information includes the associated second time;
selecting, for each time indexed sonogram image information portion, the time indexed location information that has the same second time as the first time of the sonogram image information portion;

generating a plurality of location indexed sonogram information portions based on the each one of the time indexed sonogram image information portions and the corresponding time indexed location information;

combining the received plurality of location indexed sonogram image information portions to generate a composite sonogram image information; and generating the 3D model data based on the generated composite sonogram image information.

9. The method of claim 8, wherein at least one first optical target is located on the human subject and is visible in each one of the series of captured camera images, wherein at least one second optical target that is located on the ultrasound transducer probe is visible in each one of the series captured camera images, wherein determining time indexed location information for each camera image comprises:

determining a location of the at least one first target on the human subject and a location of the at least one second target on the ultrasound transducer probe, and wherein the location of the portion of the human subject that is being scanned by the ultrasound transducer probe is determined based on the determined location of the at least one first target and the determined location of the at least one second target.

10. The method of claim 8, wherein generating a plurality of time indexed sonogram image information portions comprises:

adding the first time to the each one of the time indexed sonogram image information portions using a clock of an ultrasound image data processor; and adding the second time to the each one of the camera images using the clock of the ultrasound image data processor that receives the serial plurality of camera images.

11. The method of claim 8, further comprising:

generating 3D composite sonogram graphical information based on the generated composite sonogram image information.

12. The method of claim 11, generating a 3D image based on the 3D composite sonogram graphical information; and presenting the 3D image on a display.

13. The method of claim 8, generating a 3D image based on the 3D model data; and presenting the 3D image on a display.

14. The method of claim 8, wherein the generated 3D model data is defined as a collection of points in a 3D space corresponding to a surface of an organ or interest.

15. The method of claim 14, wherein the collection of points in the 3D space is a point cloud of geometric samples on the surface of the organ of interest.

16. The method of claim 14, wherein the organ of interest is at least a portion of a spine of the human subject.

17. The method of claim 16, wherein generating the 3D model data comprises:

generating a graphical artifact that indicates the determined at least one of position and orientation between two vertebrae of the spine; and presenting the generated graphical artifact on the presented image of the spine.

18. The method of claim 14, filtering the sonogram image information in each received portion of the ultrasound scan to discriminate the organ of interest from other surrounding organs, wherein sonogram image information associated with the other surrounding organs is removed.

* * * * *